United States Patent [19]

Chen et al.

[11] Patent Number: 5,712,411
[45] Date of Patent: Jan. 27, 1998

[54] N-VINYLFORMAMIDOPROPIONATES AND PROCESS FOR THEIR SYNTHESIS

[75] Inventors: Ning Chen, Allentown; Walter Louis Renz, Macungie; Robert Krantz Pinschmidt, Jr., Allentown; William Eamon Carroll, Orefield, all of Pa.

[73] Assignee: Air Products and Chemicals, Inc., Allentown, Pa.

[21] Appl. No.: 572,416

[22] Filed: Dec. 14, 1995

[51] Int. Cl.$^6$ .................................................. C07C 229/30
[52] U.S. Cl. ........................................... 560/172; 560/155
[58] Field of Search ..................................... 560/172, 155

[56] References Cited

U.S. PATENT DOCUMENTS

| | | | |
|---|---|---|---|
| 4,205,139 | 5/1980 | Barzynski et al. | 525/38 |
| 4,424,314 | 1/1984 | Barzynski et al. | 525/454 |
| 5,281,682 | 1/1994 | Cornforth et al. | 526/273 |
| 5,463,110 | 10/1995 | Chen et al. | 560/172 |

*Primary Examiner*—Patricia L. Morris
*Assistant Examiner*—Jean F. Vollano
*Attorney, Agent, or Firm*—Mark L. Rodgers

[57] ABSTRACT

A process is provided for the synthesis of N-vinylformamidopropionates by the reaction of NVF with acrylic and methacrylic acid esters in the presence of a metal hydride catalyst. This process allows for the improved production of mono-functional monomers and also for the synthesis of new multi-functional monomers which are useful as crosslinkers and chain extenders in photo-cure applications.

9 Claims, No Drawings

N-VINYLFORMAMIDOPROPIONATES AND PROCESS FOR THEIR SYNTHESIS

TECHNICAL FIELD OF THE INVENTION

The invention relates to a new process for the reaction of N-vinylamides with acrylates, and specifically for the synthesis of multi-functional monomers useful as chain extenders and crosslinking agents in preparing crosslinked polymers. This invention has particular application to photocurable coatings.

BACKGROUND OF THE INVENTION

In conventional radiation cure processes, acrylate terminated urethane or epoxy resins are mixed with di-, tri-, or tetra functional crosslinkers, typically di-, tri-, or tetraacrylate esters of small polyhydroxy compounds. These are then diluted to desired viscosity with monovinyl functional compounds (reactive diluents) and, on polymerization, constitute the backbone of the polymer coating obtained. Additional components in the compositions may include dyes, fillers, pigments, adhesion promoters, wetting agents and other additives, and, usually one or more free radical initiator and various coinitiators. On exposure to light of appropriate wavelengths, frequently 200 to 400 nm, the system polymerizes rapidly to a hard, high performance, chemically resistant, crosslinked coating, adhesive, binder, or ink with a minimum of volatile organic emissions.

However, acrylates have high toxicity and very strong odor before polymerization. It has become necessary to find replacements for the acrylate terminated resins, the polyacrylate functional crosslinkers, and the reactive diluent which have lower toxicity and odor.

Unsaturated monomers of the N-vinylamide class have been employed in free radical polymerization reactions for the preparation of homopolymers and copolymers having a range of useful properties.

Several N-vinylamides have been found to be useful as components in photopolymerizable compositions of various types. As a class, the vinylamides possess acceptable photopolymerization rates, good compatibility with other components in various photocurable formulations, copolymerizability with acrylates, comparative resistance to oxygen inhibition, favorable adhesion-promoting properties, lower volatility and odor, and relatively low toxicity.

Cornforth et al. U.S. Pat. No. 5,281,682 teach improved radiation-curable formulations containing N-vinylformamide and an oligomer selected from the group epoxy acrylates, urethane acrylates, polyester acrylates and mixtures thereof.

Multifunctional monomers, which provide high cure speed and high crosslink density needed for hard, chemically resistant films, but which do not contain toxic acrylate functionality are rare. These materials should have low volatility, be liquid or readily soluble in reactive diluents, have good color and stability, and cure rapidly with limited oxygen inhibition to hard, chemically resistant coatings. Barzynski et al. U.S. Pat. Nos. 4,205,139 and 4,424,314 teach compositions containing N-vinyl compounds in which at least two N-vinyl groups are present and in which at least one carbonyl group is bound to the nitrogen of the N-vinyl group, said carbonyl group in turn being bonded to a nitrogen or carbon atom.

Chen et al., U.S. Pat. No. 5,463,110, teach the synthesis of a family N-vinylformamide derivatives prepared by the reaction of NVF with acrylate and methacrylate esters under base catalysis, preferably using metal alkoxide catalysts. These adducts offer improved stability and performance in radiation cure coatings as reactive diluents. This patent further suggests reaction of NVF with acrylates and methacrylates obtained by esterification of alcohols having hydroxyl functionalities from 2 to about 6, but the inventors were not able at that time to achieve the desired reaction. Furthermore, the primary product mixtures prepared from NVF and alkyl esters of acrylic or methacrylic acid under the influence of the claimed base catalysts were highly colored and required an expensive and sometimes problematic high vacuum distillation to remove the low volatility, yet reactive N-vinylamides from the color bodies. 3-N-Vinylformamidopropionates of heavier alcohols become progressively more difficult to distill and thus obtain with sufficiently good color for commercial use in a practical process. Other techniques for decolorization were either ineffective or prohibitively expensive. The very high boiling points of di- or higher N-vinylformamide functional derivatives make them effectively nondistillable and thus impractical even if they could be made via the then available process.

One object of the present invention is to provide a process for the reaction of N-vinylamides, and in particular, N-vinylformamide, with acrylate esters to prepare 3-N-vinylformamidopropionates with less initial color and in high yield. It is further the object of this invention to provide novel di- and higher N-vinylamide functional crosslinking monomers, available by this new process, which simultaneously exhibit the desirable solvent or solution properties, the good polymerization properties, and the desirable physical properties of N-vinylamides, plus the ability to rapidly form high performance, solvent resistant crosslinked coatings, inks, binders and adhesives when used as crosslinking monomers in a radiation cure formulation.

SUMMARY OF THE INVENTION

It has now been found, surprisingly, that the use of a metal hydride as a catalyst in the reaction of N-vinylformamide (NVF) with acrylate esters cures the defects in the prior art processes by improving color in the reaction and producing product in high yield. Additionally, the use of these catalysts allows for the first time the synthesis of di- or higher N-vinylformamidopropionates from NVF and di- or higher acrylate esters. These novel multi-vinylamide compositions prepared by this process have been demonstrated to show excellent performance as crosslinkers in practical radiation cure formulations.

The process of the present invention involves the addition of N-vinylformamide to acrylic or methacrylic acid esters to give 3-(N-vinylformamido)propionates and 2-methyl-3-(N-vinylformamido)propionates using a metal hydride as the catalyst in the reaction. In addition to improving the yield, color, and purity of the subject reaction, the improved process allows for the first time the synthesis of novel di- and higher N-vinylformamido functional monomers. The new N-vinylformamidopropionates encompassed by this invention can be represented by the general structural formula:

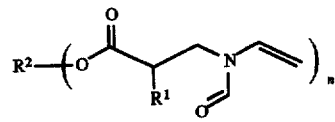

Where $R^1$ is hydrogen or methyl and $R^2$ is derived from a polyhydroxy linear or branched alkyl, cycloalkyl, arylalkyl, alkyloxyalkyl, oligoalkyleneoxy or aryl group containing from 1 to about 20 carbon atoms and n is from 2 to 5.

The base catalyst used in the present process is a metal hydride, such as an alkali metal hydride, an alkaline earth metal hydride, or the hydride of a different metal or metalloid element. The reaction is performed either in a mixture of the neat monomers or in a suitable organic solvent at a temperature between 0° and 100° C. The reaction is allowed to proceed for a period between 1 and 100 hours, after which time the product is recovered, preferably by distillation of solvent, but optionally also by vacuum distillation of the product, where that is feasible.

DETAILED DESCRIPTION OF THE INVENTION

The process of the present invention involves the addition of N-vinylformamide to acrylic or methacrylic acid esters to give 3-(N-vinylformamido)propionates and 2-methyl-3-(N-vinylformamido)propionates in the presence of a metal hydride catalyst. In addition to improving the yield, color, and purity of the prior art reaction of NVF with simple acrylate esters to produce mono-functional N-vinylformamidopropionates, the improved process allows for the synthesis of novel di- and higher N-vinylformamido functional monomers. The new multi-functional monomers encompassed by this invention have the general structure:

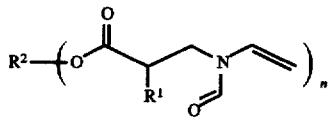

Where $R^1$ is hydrogen or methyl and $R^2$ is derived from a polyhydroxy linear or branched alkyl, cycloalkyl, arylalkyl, alkyloxyalkyl, oligoalkyleneoxy or aryl group containing from 1 to about 20 carbon atoms and n is from 2 to 5.

The reaction can be run at less than full conversion or with less than a full equivalent of vinylamide for each acrylate or methacrylate group in a poly(meth)acrylate functional monomer. In such cases, the product will contain a mixture of vinylamide and acrylate or methacrylate groups.

The key to the present invention is the use of a base catalyst comprising a metal hydride, such as an alkali metal hydride or an alkaline earth metal hydride. Hydrides and mixed alkyl hydrides of aluminum or boron or of a different metal or metalloid element may also be useful in this reaction. Examples include lithium tetrahydridoaluminum, sodium or other alkali metal salts of tetrahydridoborane, hydridoboranes and hydridoaluminum compounds with alkyl or alkoxide or other substituents.

The reaction is performed either in a mixture of the neat monomers or in a suitable organic solvent, or with a heel of the product at a temperature between 0° and 100° C. The reaction may be run batch or with delay feeds of the vinylamide and acrylate or methacrylate. Preferred solvents include ethers such a diethyl ether, methyl tert-butyl ether, tetrahydrofuran, or ethyleneglycol dimethyl ether; esters such as ethyl or butyl acetate; aromatics such as benzene, toluene, xylene or anisole; and nitriles such as acetonitrile. Less preferred are chlorinated hydrocarbons and alkanes.

Compounds prepared according to this invention where n=1 have been previously found to be useful as monomers, especially as reactive diluents in photocurable coatings and as comonomers in coatings, adhesives and binders. Compounds where n=at least 2 demonstrate excellent solvent or solution properties, low viscosity, low vapor pressure, low color, and high cure speed in free radical photopolymerization. They provide excellent solvent resistance, hardness, and appearance to the crosslinked photoproduct.

It is recognized by the inventors that, while useful in radiation curing, the di- and higher vinylformamide functional monomers of the present invention may have broader utility in other types of polymer synthesis, such as bulk, suspension, emulsion or solution polymerization and that they will polymerize with monomers different from those commonly used in radiation-curing (e.g., ethylene, vinyl acetate, vinyl chloride, maleate esters, acrylonitrile, etc.). Accordingly, the present invention is intended to subsume the homopolymerization or copolymerization of these monomers by any means known in the art.

The following examples are presented to better illustrate the present invention and are not meant to be limiting.

EXAMPLE 1

Preparation of 1,4-butanediol di-[3-(N-vinylformamido) propionate] (BDNVFP)

To a 500 mL three-neck round bottom flask equipped with a condenser and a stirrer was added 1.6 g of 60% sodium hydride in mineral oil. The sodium hydride was washed with hexane twice and the solvent was decanted. Under nitrogen, 50 grams of methyl t-butyl ether were added in one portion. With vigorous stirring, a mixture of 104.25 grams of butanediol diacrylate and 74.7 grams of NVF was added in 10 min. After the addition, the mixture was stirred at room temperature for 24 hours. The mixture was then neutralized with acetic acid and filtered through a silica gel layer (~0.5 cm). The filtrate was placed on a rotary evaporator. Solvent was removed at 45° C. to give 141 grams (78.8%) of pale yellow liquid.

EXAMPLE 2

Preparation of 1,6-hexanediol di-[3-(N-vinylformamido) propionate] (HDNVFP)

To a 100 mL three-neck round bottom flask equipped with a condenser and stirrer was added 0.16 g of 60% sodium hydride in mineral oil. The sodium hydride was washed with hexane twice and the solvent was decanted. Under nitrogen, 4 grams of methyl t-butyl ether were added in one portion. With vigorous stirring, a mixture of 22.6 grams of hexanediol diacrylate and 14.2 grams of NVF was added in 2 min. After the addition, the mixture was stirred at room temperature for one hour. The mixture was then neutralized with acetic acid and filtered through a silica gel layer (~0.2 cm). The filtrate was placed on a rotary evaporator. Solvent was removed at 45° C. to give 29.1 grams (79.0%) of pale yellow liquid.

EXAMPLE 3

Preparation of 1,6-hexanediol di-[3-(N-vinylformamido) propionate] (HDNVFP) with Potassium Hydride To a 100 mL three-neck round bottom flask equipped with a condenser and stirrer was added 0.26 g of potassium hydride in mineral oil. The potassium hydride was washed with hexane twice and the solvent was decanted. Under nitrogen and with vigorous stirring, a mixture of 22.6 grams of hexanediol diacrylate and 14.1 grams of NVF was added in 3 min. After the addition, the mixture was stirred at room temperature for two hours. The mixture was then neutralized with acetic acid and filtered through a silica gel layer (~0.2 cm) to give 28.2 grams (77.0%) of pale yellow liquid (Gardner color scale=1).

EXAMPLE 4

Preparation of 1,6-hexanediol di-[3-(N-vinylformamido) propionate] (HDNVFP) with Calcium Hydride To a 100 mL three-neck round bottom flask equipped with a condenser and stirrer was added 0.30 g of dry calcium hydride. Under nitrogen and with vigorous stirring, a mixture of 22.6 grams of hexanediol diacrylate and 14.2 grams of NVF was added in 1 min. After the addition, the mixture was stirred at room temperature for two hour and sample was collected and examined by NMR. $^1$H NMR showed that only ~20% of conversion was obtained. However, after 21 hours, the conversion was increased to ~62%, by NMR analysis.

EXAMPLE 5

Preparation of Trimethylolpropane Tri-[3-(N-vinylformamido)propionate] (TMPNVFP) with Potassium Hydride To a 100 mL three-neck round bottom flask equipped with a condenser and stirrer was added 0.40 g of potassium hydride in mineral oil. The potassium hydride was washed with hexane twice and the solvent was decanted. Under nitrogen and with vigorous stirring, a mixture of 29.6 grams of trimethylolpropane triacrylate and 21.3 grams of NVF in 30 mL of THF was added in 3 min. After the addition, the mixture was stirred at room temperature for 20 hours. The mixture was then neutralized with acetic acid and filtered through a silica gel layer (~0.2 cm). The filtrate was placed on a rotary evaporator. Solvent was removed and the mixture was analyzed by NMR. $^1$H NMR showed that ~25% of the triacrylates were functionalized with NVF.

EXAMPLE 6

Preparation of Methyl 3-N-vinylformamido-2-methylpropionate with Potassium Hydride Catalyst To an inserted 100 mL three-neck round bottom flask equipped with a condenser, thermocouple, magnetic stirrer, nitrogen inlet, and addition funnel was added 0.54 g of potassium hydride in mineral oil via a hexane rinse. The hexane was removed with a pipet and a mixture of 20.0 g (0.2 mole) of methyl methacrylate and 14.2 g (0.2 mole) of N-vinylformamide was added slowly via the addition funnel. An initial exotherm was followed by an induction period, but after warming to 40° C. and adding a small additional amount of KH, a gentle exotherm began. The reaction rate could be increased by raising the temperature. The reaction generated the expected product as confirmed by gas chromatography in a smooth, easily controlled reaction with good color.

EXAMPLE 7

Preparation of 1,4-butanediol di-[3-(N-vinylformamido) propionate] (BDNVFP) with Butyl Lithium (Comparative)

To a 100 mL three-neck round bottom flask equipped with a condenser and a stirrer was added 19.8 grams of butanediol diacrylate and 14.2 grams of NVF. After the addition, the mixture was stirred at room temperature for 5 minutes. Then 0.1 mL of butyl lithium was added to the solution. After two hours, sample was collected and by NMR. $^1$H NMR indicated very low conversion at this point. Then 0.5 mL of butyl lithium was added to the reaction mixture and allowed the reaction to continue for 18 more hours. At the end of 20 hour reaction, a half gel/half liquid mixture was obtained. The liquid part contained ~70% of the desired product. The gel part was not soluble in THF. When this mixture was allowed to stand at room temperature, more insoluble materials formed and they were proportional to the standing time.

EXAMPLE 8

Preparation of 1,2-Ethylene Glycol di-[3-(N-vinylformamido)propionate] (EGNVFP) with Butyl Lithium (Comparative)

To a 100 mL three-neck round bottom flask equipped with a condenser and a stirrer was added 17.3 grams of butanediol diacrylate and 14.4 grams of NVF. After the addition, the mixture was stirred at room temperature for 5 minutes. Then 1 mL of butyl lithium was added to the solution. After fifteen hours, sample was collected and examined by NMR. $^1$H NMR indicated only ~24% conversion. Accompanying with the product, a large amount of insoluble polymer was formed. More catalyst and extended reaction time did not improve the yield of the desired product.

EXAMPLE 9

Attempted Preparation of 1,4-butanediol di-[3-(N-vinylformamido)propionate] (BDNVFP) with Sodium Methoxide (Comparative)

To a 100 mL three-neck round bottom flask equipped with a condenser and a stirrer was added 19.8 grams of butanediol diacrylate and 14.2 grams of NVF. After the addition, the mixture was stirred at room temperature for 5 minutes. Then 0.2 mL of sodium methoxide was added to the solution. After 20 hours, sample was collected and examined by NMR. $^1$H NMR showed there was no desired product formed.

EXAMPLE 10

The relative performance of the NVF/diacrylate esters as chain extenders or crosslinkers in photopolymerizable compositions was assessed by comparison with diacrylates of the prior art. Equal weight fractions of the N-vinyl compounds were compared in a model formulation containing an epoxy acrylate oligomer, one tri-functional acrylate monomer and a common free radical photoinitiator.

| Component | Weight % |
|---|---|
| Epoxy diacrylate oligomer[1] | 50% |
| TMPTA[2] | 10% |
| di-N-vinyl ester | 10% |
| N-vinyl monomers[3] | 30% |
| Irgacure 184[4] | 2.5 phr (based on weight of the above) |

[1]Ebecryl TM 3700 (UCB Radcure)
[2]Trimethylopropane triacrylate (UCB Radcure)
[3]NVF or it Michael adducts
[4]1-Hydroxycyclohexyl phenyl ketone (Ciba-Geigy)

The liquid mixture comprising the oligomer, acrylate trimer, N-vinyl terminated dimer, N-vinyl monomer, and photoinitiator were mixed well and the Brookfield viscosity was measured. Thin films were drawn down on cleaned 5"×20" aluminum panels using a #10 wire bar. The panel were cured under ultraviolet light in air using a commercial 300 watt/inch medium pressure mercury lamp and conveyor system. Cured film properties were assessed after a single exposure at a conveyor speed of 105 feet per min.

The extent of cure was indicated by measuring the water and solvent resistance of the films using the double rub test. Film hardness was evaluated by the Persoz hardness technique using a BYK Gardner Pendulum Hardness Tester calibrated on glass. Relative cure speed of each formulation was evaluated using a depth of cure comparator (UV Process Supply Inc.).

Using N-vinylformamide as the reactive diluent, the properties of the formulation containing di-N-vinyl esters of this invention and for comparison, a formulation containing commercial TRPGA (tripropyleneglycol diacrylate) are listed in Table 1.

TABLE 1

|  | TRPGDA | BDNVFP | HDNVFP |
|---|---|---|---|
| Formulation viscosity (cps, 25° C.) | 162 | 272 | 220 |
| Film thickness (mils) | 4.0 | 4.0 | 3.4 |
| Persoz hardness (second) | 255 | 191 | 258 |
| Water double rubs | >200 | >200 | >200 |
| MEK double rubs | >200 | >200 | >200 |

Using methyl 3-(N-vinylformamido)propionate as the reactive diluent, the properties of the formulation containing di-N-vinyl esters of this invention and for comparison, a formulation containing commercial TRPGA (tripropyleneglycol diacrylate) are listed in Table 2.

TABLE 2

|  | TRPGDA | BDNVFP | HDNVFP |
|---|---|---|---|
| Formulation viscosity (cps, 25° C.) | 330 | 708 | 564 |
| Film thickness (mils) | 4.0 | 3.6 | 3.6 |
| Persoz hardness (second) | 159 | 146 | 152 |
| Water double rubs | >200 | >200 | >200 |
| MEK double rubs | >200 | >200 | >200 |

Having thus described the present invention, what is now deemed appropriate for Letters Patent is set out in the following appended claims.

We claim:
1. A process for preparing N-vinylformamidopropionates comprising reacting N-vinylformamide with an acrylic or methacrylic acid ester in the presence of a metal hydride catalyst.
2. A process in accordance with claim 1 wherein said catalyst is an alkali metal hydride.
3. A process in accordance with claim 1 wherein said catalyst is an alkaline earth metal hydride.
4. A process in accordance with claim 1 wherein said reaction is carried out in a mixture of the neat monomers.
5. A process in accordance with claim 1 wherein said reaction is carried out in an organic solvent.
6. A process in accordance with claim 5 wherein said organic solvent is selected from the group consisting of ethers such as diethyl ether, methyl tert-butyl ether, tetrahydrofuran, or ethyleneglycol dimethyl ether; esters such as ethyl or butyl acetate; aromatics such as benzene, toluene, xylene or anisole; and nitriles such as acetonitrile.
7. A process in accordance with claim 1 wherein said reaction is carried out at a temperature from 0° C. to 100° C. for between 1 and 100 hours.
8. A process in accordance with claim 1 wherein said N-vinylformamidopropionates have the structural formula:

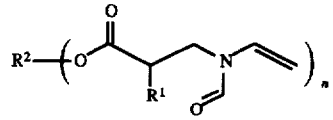

Where $R^1$ is hydrogen or methyl and $R^2$ is derived from a polyhydroxy linear or branched alkyl, cycloalkyl, arylalkyl, alkyloxyalkyl, oligoalkyleneoxy or aryl group containing from 1 to about 20 carbon atoms, such that n=1 to about 5.
9. A process in accordance with claim 1 wherein said N-vinylformamide is reacted with butanediol diacrylate or hexanediol diacrylate.

* * * * *